(12) United States Patent
Eltorai et al.

(10) Patent No.: US 10,967,197 B2
(45) Date of Patent: Apr. 6, 2021

(54) PHOTOTHERAPY DEVICES AND METHODS FOR TREATING TRUNCAL ACNE AND SCARS

(71) Applicant: Azulite, Inc., Old Saybrook, CT (US)

(72) Inventors: Adam E. M. Eltorai, Old Saybrook, CT (US); Daniel Gertrudes, Providence, RI (US); Don Nguyen, Warwick, RI (US)

(73) Assignee: Azulite, Inc., Old Saybrook, CT (US)

( * ) Notice: Subject to any disclaimer, the term of this patent is extended or adjusted under 35 U.S.C. 154(b) by 29 days.

(21) Appl. No.: 16/116,518

(22) Filed: Aug. 29, 2018

(65) Prior Publication Data

US 2020/0069964 A1 Mar. 5, 2020

(51) Int. Cl.
*A61N 5/06* (2006.01)
*F21K 9/23* (2016.01)
*F21Y 115/10* (2016.01)

(52) U.S. Cl.
CPC .... *A61N 5/0616* (2013.01); *A61N 2005/0642* (2013.01); *A61N 2005/0643* (2013.01);
(Continued)

(58) Field of Classification Search
CPC .......... A61N 5/0616; A61N 2005/0652; A61N 2005/0643; A61N 2005/0642; F21Y 2115/10; F21K 9/23
See application file for complete search history.

(56) References Cited

U.S. PATENT DOCUMENTS 5,616,140 A * 4/1997 Prescott ............... A61N 5/0616 606/10
6,290,713 B1 9/2001 Russell
(Continued)

FOREIGN PATENT DOCUMENTS

AU 200066468 B2 3/2001
AU 2014231590 A1 10/2015
(Continued)

OTHER PUBLICATIONS

Pina Avci et al. "Low-level laser (light) therapy (LLLT) in skin: stimulating, healing, restoring." Seminars in cutaneous medicine and surgery vol. 32,1 (2013): 41-52, https://www.ncbi.nlm.nih.gov/pmc/articles/PMC4126803/, viewed on Feb. 2, 2019.*
(Continued)

*Primary Examiner* — Christopher Koharski
*Assistant Examiner* — James Moss
(74) *Attorney, Agent, or Firm* — Barlow, Josephs & Holmes, Ltd.

(57) ABSTRACT

Phototherapy devices for the treatment of truncal acne and scars include, for example, a body portion having a bottom surface and a top surface that is configured to hang on a person's shoulders and cover the upper back and/or chest. The body portion further having left and right shoulder portions extending forwardly from the body portion and curled downwardly to hook over a person's shoulders. The shoulder portions further define a space for a person's neck therebetween. A phototherapy lighting component is configured to emit a light from the bottom surface of the body portion and forwardly extending shoulder portions. In use, the person places the shoulder portions on their shoulders with the body portion hanging downwardly against the person's back or chest, for example, wearing the body portion like a cape or bib. Using the lighting component, a therapeutic amount of light is administered to the person.

9 Claims, 15 Drawing Sheets

(52) U.S. Cl.
CPC ........ *A61N 2005/0652* (2013.01); *F21K 9/23* (2016.08); *F21Y 2115/10* (2016.08)

(56) References Cited

U.S. PATENT DOCUMENTS

| | | |
|---|---|---|
| 6,600,951 B1 | 7/2003 | Anderson |
| 6,887,260 B1 | 5/2005 | McDaniel |
| 6,897,238 B2 | 5/2005 | Anderson |
| 7,018,396 B2 | 3/2006 | Sierra et al. |
| 7,118,563 B2 | 10/2006 | Weckwerth et al. |
| 7,198,634 B2 | 4/2007 | Harth et al. |
| 7,201,765 B2 | 4/2007 | McDaniel |
| 7,250,045 B2 | 7/2007 | Island et al. |
| 7,413,567 B2 | 8/2008 | Weckwerth et al. |
| 7,452,356 B2 | 11/2008 | Grove et al. |
| 7,494,503 B2 | 2/2009 | McDaniel |
| 7,556,820 B2 | 7/2009 | Ramirez et al. |
| 8,337,809 B2 | 12/2012 | Yu et al. |
| 8,551,104 B2 | 10/2013 | Weckwerth et al. |
| 8,647,372 B2 | 2/2014 | Kang et al. |
| 8,685,017 B2 | 4/2014 | Stern et al. |
| 8,709,003 B2 | 4/2014 | Island et al. |
| 8,771,263 B2 | 7/2014 | Epshtein et al. |
| 8,777,935 B2 | 7/2014 | Weckwerth et al. |
| 8,795,635 B2 | 8/2014 | Tamarkin et al. |
| 8,808,753 B2 | 8/2014 | Palladino et al. |
| 8,821,940 B2 | 9/2014 | Harris et al. |
| 8,834,933 B2 | 9/2014 | Harris et al. |
| 8,858,607 B1 | 10/2014 | Jones |
| 8,911,791 B2 | 12/2014 | Piergallini et al. |
| 8,936,593 B2 | 1/2015 | Epshtein et al. |
| 8,938,295 B2 | 1/2015 | Baird et al. |
| 8,979,775 B2 | 3/2015 | Schafer et al. |
| 9,061,056 B2 | 6/2015 | Harris et al. |
| 9,079,022 B2 | 7/2015 | Baird et al. |
| 9,084,587 B2 | 7/2015 | Eckhouse et al. |
| 9,211,259 B2 | 12/2015 | Friedman et al. |
| 9,249,334 B2 | 2/2016 | Oldenburg et al. |
| 9,278,230 B2 | 3/2016 | Levin et al. |
| 9,295,855 B2 | 3/2016 | Jones et al. |
| 9,295,858 B2 | 3/2016 | Rosenberg |
| 9,314,293 B2 | 4/2016 | Rosenberg |
| 9,428,582 B2 | 8/2016 | Edvardsen et al. |
| 9,439,965 B2 | 9/2016 | Harris et al. |
| 9,498,650 B2 | 11/2016 | Schafer et al. |
| 9,572,880 B2 | 2/2017 | Harris et al. |
| 2004/0008523 A1* | 1/2004 | Butler .................. A61N 5/0613 362/551 |
| 2009/0076170 A1 | 3/2009 | Ramirez et al. |
| 2009/0227996 A1 | 9/2009 | Powell et al. |
| 2009/0254156 A1 | 10/2009 | Powell et al. |
| 2009/0306023 A1 | 12/2009 | Ramirez et al. |
| 2014/0121732 A1 | 5/2014 | Goren et al. |
| 2014/0155962 A1* | 6/2014 | Deroberts ............. G06F 3/0484 607/89 |
| 2014/0276354 A1 | 9/2014 | Piergallini et al. |
| 2014/0323950 A1 | 10/2014 | Wirth |
| 2014/0324137 A1 | 10/2014 | Tapper et al. |
| 2015/0217142 A1 | 8/2015 | Schafer |
| 2015/0265846 A1 | 9/2015 | Baird et al. |
| 2015/0335909 A1 | 11/2015 | Tapper et al. |
| 2015/0361500 A1 | 12/2015 | Chang et al. |
| 2016/0016001 A1 | 1/2016 | Loupis et al. |
| 2016/0030564 A1 | 2/2016 | Loupis et al. |
| 2016/0045759 A1 | 2/2016 | Tapper et al. |
| 2016/0051834 A1 | 2/2016 | Tapper et al. |
| 2016/0199492 A1 | 7/2016 | Wirth |
| 2017/0014640 A1* | 1/2017 | Kariguddaiah ......... A61F 5/028 |
| 2017/0027833 A1 | 2/2017 | Piergallini et al. |
| 2018/0015297 A1* | 1/2018 | Kahn .................... A61N 5/0613 |
| 2018/0236258 A1* | 8/2018 | Dotson .................... A61B 3/12 |

FOREIGN PATENT DOCUMENTS

| | | |
|---|---|---|
| AU | 2015273123 A1 | 12/2016 |
| AU | 2015274201 A1 | 12/2016 |
| AU | 2015281804 A1 | 1/2017 |
| BR | 102012019268-3 A2 | 3/2016 |
| CA | 2848136 A1 | 3/2013 |
| CA | 2902363 A1 | 9/2014 |
| CA | 2951056 A1 | 12/2015 |
| CA | 2951467 A1 | 12/2015 |
| CA | 2951513 A1 | 12/2015 |
| CA | 2952954 | 12/2015 |
| CN | 101862507 A | 10/2010 |
| CN | 203072061 U | 7/2013 |
| CN | 203072062 U | 7/2013 |
| CN | 103930162 A | 7/2014 |
| CN | 103933667 A | 7/2014 |
| CN | 103945150 A | 7/2014 |
| CN | 105163759 A | 12/2015 |
| CN | 105451815 A | 3/2016 |
| CN | 105534634 A | 5/2016 |
| CN | 103945151 A | 7/2017 |
| DE | 102011117364 A1 | 5/2013 |
| EP | 1100366 A1 | 5/2001 |
| EP | 2905544 A1 | 8/2015 |
| EP | 1924323 B1 | 8/2016 |
| EP | 2968561 A4 | 2/2017 |
| EP | 2753400 B1 | 5/2017 |
| IN | 2014DN02276 | 7/2014 |
| JP | 2012502696 A | 2/2012 |
| JP | 2014532672 A | 12/2014 |
| JP | 2016511672 A | 4/2016 |
| JP | 2016514000 A | 5/2016 |
| JP | 2016528263 A | 9/2016 |
| KR | 100944895 B1 | 3/2010 |
| KR | 101083061 B1 | 11/2011 |
| KR | 20150143456 A | 12/2015 |
| KR | 20160045856 A | 4/2016 |
| TW | 201609181 A | 3/2016 |
| WO | 2010053974 A3 | 5/2010 |
| WO | 2016092493 A1 | 6/2016 |
| WO | 2016146778 A1 | 9/2016 |
| WO | 2016168385 A2 | 10/2016 |

OTHER PUBLICATIONS

Thiboutot, D., and Zaenglein, A., "Pathogenesis, clinical manifestations, and diagnosis of acne vulgaris", Wolters Kluwer, 2014 UpToDate.

Saedi, N., and Uebelhoer, N., "Management of Acne Scars,", Wolters Kluwer, updated Aug. 22, 2017 UpToDate.

Dover, J. S., and Batra, P., "Light-based, adjunctive, and other therapies for acne vulgaris," Wolters Kluwer, updated Nov. 30, 2017 UpToDate.

Graber, E., "Hormonal therapy for women with acne vulgaris," Wolters Kluwer, updated Jun. 6, 2016 UpToDate.

Owen, C., "Oral isotretinoin therapy for acne vulgaris," Wolters Kluwer, updated Aug. 29, 2017 UpToDate.

Graber, E., "Treatment of acne vulgaris," Wolters Kluwer, updated Aug. 10, 2017 UpToDate.

Hruza, G., "Principles of laser and intense pulsed light for cutaneous lesions," Wolters Kluwer, updated Mar. 13, 2017 UpToDate.

Del Rosso, J., "Management of Truncal Acne Vulgaris: Current Perspectives on Treatment," Drug Therapy Topics, vol. 77, May 2006.

\* cited by examiner

PHOTOTHERAPY DEVICES AND METHODS FOR TREATING TRUNCAL ACNE AND SCARS

BACKGROUND OF THE INVENTION

Field of the Invention

The present patent document relates generally to devices for the application phototherapy treatments to a patient and more particularly to a phototherapy apparatus for truncal acne and method of treatment.

Background of the Related Art

Acne vulgaris is a common cutaneous disorder which can affect adolescents and young adults alike. Body, or truncal, acne can present on all portions of a patient's torso including the back and chest. Patients that suffer from this condition can experience significant scarring of the skin which can result in psychological side-effects. Thus, there has been much research into prevention of acne vulgaris and reduction of the resulting scarring.

Body or truncal acne is currently primarily treated with topical oral medications, which can have harmful side effects, adverse reactions, or other disadvantages. Common treatments may include over-the-counter medications applied on the skin, such as benzoyl peroxide; prescription acne medications applied on the skin, such as topical retinoids and antibiotics; and oral prescription medications, such as oral antibiotics, isotretinoin, and oral contraceptives.

There are also a number of homeopathic remedies, such as applying to the affected area one or more of a paste of baking soda, diluted apple cider vinegar applied with a spray bottle, lemon juice applied by a halved lemon, a mixture of honey and oats, or aloe vera. However, these home remedies are messy and often require repeated applications two-three times daily.

In addition to the topical or oral medications and homeopathic remedies, the prior art has recognized certain benefits of light treatment of truncal acne. Clinician-administered light sources are used for the treatment of acne. Examples of light-based therapies include: broad-spectrum continuous-wave visible light sources (blue light, red light); intense pulsed light; laser sources including the potassium titanyl phosphate (KTP) laser, pulsed dye laser (PDL), and infrared lasers, photodynamic therapy; and photopneumatic technology. Clinician-administered light sources can be complex systems which require extensive training to use. At home light base therapies can suffer from several deficiencies including the need for the user to hold the device in place for the entirety of the light therapy, thereby limiting the user to the use of one free hand—at best. However, light-based treatments are safe, effective, and have minimal complication when used correctly.

Furthermore, acne on large areas of the body or hard-to-reach spots, such as the back, may make it difficult to apply topical acne medications and/or remedies. Some topical acne treatments may also discolor or bleach clothing. Left untreated, though, truncal acne may lead to a type of scarring called follicular macular atrophy.

As a result, there is a further need to prevent and treat scarring, including follicular macular atrophy. Current treatments include traditional ablative laser resurfacing, non-ablative fractional laser resurfacing, other collagen remodeling procedures, ablative fractional laser resurfacing, chemical peels, dermabrasion, skin needling, fractional bipolar radiofrequency, and combinations thereof.

As noted above, there are major challenges when treating truncal acne vulgaris involves extensive body surface area. This factor may complicate treatment with topical therapy. Certain vehicles, such as foams, lotions, and some water-based gels, may be more applicable for truncal application, provided the specific formulation exhibits ease of spreadability, rapid cutaneous penetration, effective drug delivery, and lack of residue. Moreover, scarring is not an uncommon consequence of truncal acne vulgaris. Although scarring is more likely to occur after resolution of deep inflammatory (nodular) acne lesions, scarring may occur in association with acne lesions of any type or severity. A form of acne scarring that occurs almost exclusively on the trunk and upper arms is follicular macular atrophy. Many patients with scarring related to truncal acne vulgaris are bothered by the appearance of this form of atrophic scarring. Unfortunately, a consistently effective treatment regimen for truncal acne scarring is not available. Further, at home management of truncal acne can be mechanically difficult to reach.

Thus, there is a need for safe and effective therapies for truncal acne and scarring. Therefore, there is a perceived need for a method of treating truncal acne that does not require oral medications, the application of messy topical treatments, or clinician applied treatments.

SUMMARY OF THE INVENTION

The present invention describes methods and apparatuses for applying phototherapy to the body for treating truncal acne that solves the problems of the prior art. The method and apparatus can, for example, be used to treat acne on the back, chest, or both.

In one exemplary embodiment, the phototherapy methods and apparatuses can include a body portion having a bottom surface and a top surface that is configured to hang on a person's shoulders and cover the upper back or chest. The body portion can further have left and right shoulder portions extending forwardly from the body portion and curled downwardly to hook over a person's shoulders. The left and right shoulder portions can further define a space for a person's neck therebetween. A lighting component can be configured and arranged to emit a light from the bottom surface of the body portion and forwardly extending left and right shoulder portions. In one exemplary method of use, the user can place the left and right shoulder portions on their shoulders with the body portion hanging downwardly against the person's back, wearing the body portion like a cape. In an alternative, the user can place the apparatus on their body such that the body portion covers their chest, wearing apparatus like a bib. In a further alternative, the apparatus can include body portions that can cover both the back and chest of the user at the same time. The apparatus may further include standoffs on the bottom surface of the body and shoulder portions, to elevate the bottom surface, and thus the lights, away from the user's skin. Consequently, the light emitted from the lighting component covers a wider area of the user's trunk.

Using the lighting component, a therapeutic amount of light can be administered to the user with the apparatus. The administered light can preferably be non-UV light, but may be any therapeutic light, including those discussed above, that is suitable for treating acne or scarring. The administered light may be for any period of time, for example, twenty to thirty minutes, during weekly intervals, or other treatment regimens as determined by the treatment regimen, such as by a medical professional.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENT

Referring to FIGS. 1-7, an exemplary embodiment of a phototherapy apparatus for the treatment of truncal acne is illustrated generally at 10. The apparatus generally includes a body portion 12 having a bottom surface 14 and a top surface 16 that is configured to hang on a person's shoulders and cover the upper back. The body portion is preferably made of molded of plastic but may be formed in any way of any type of material, such as thermoformed or three-dimensionally printed plastic or other materials. The body portion 12 may also be made of metal and can be cast or press-formed by way of example.

Figure 7A:
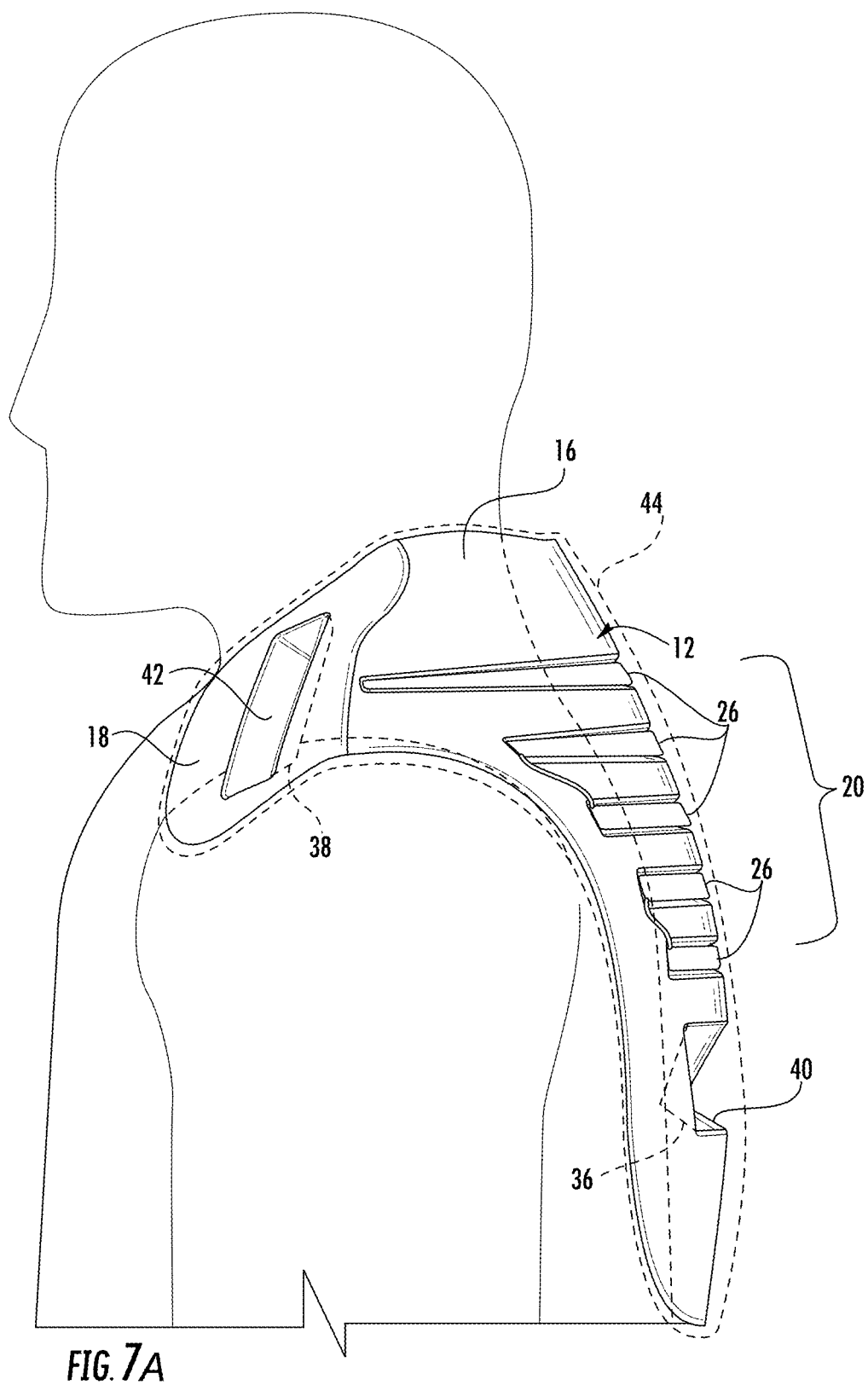
FIG. 7A is a side view of an exemplary environment with the apparatus in place on a person.
Figures 9A, 9B:
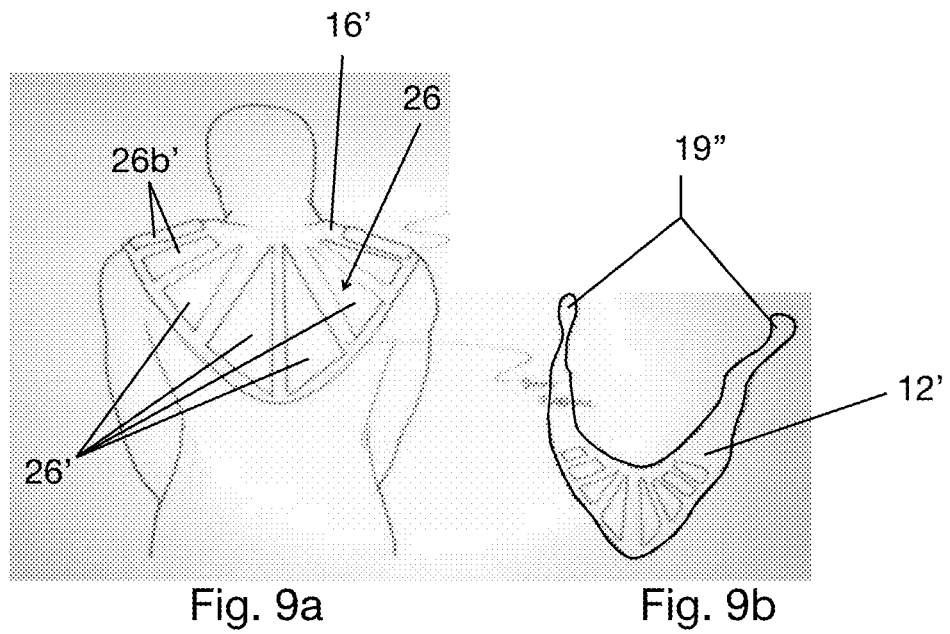
FIGS. 9a-c show various views of a further exemplary embodiment.
Figure 9C:
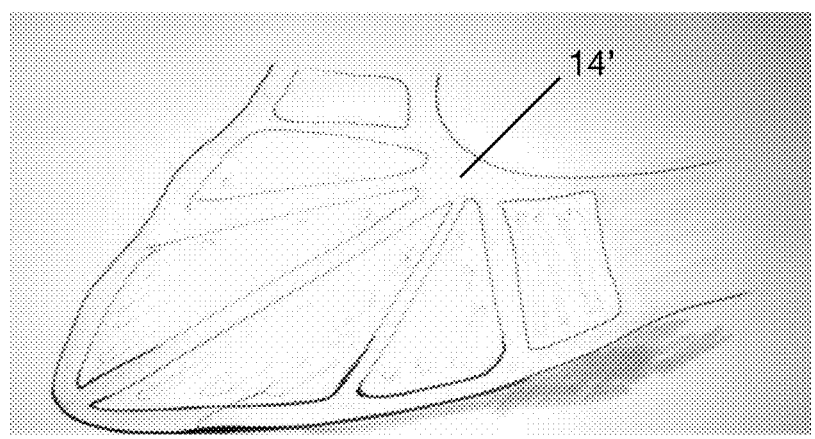

The body portion 12 further has left and right shoulder portions 18 extending forwardly from the body portion 12 and curled downwardly to hook over a person's shoulders. The left and right shoulder portions 18 further define a space for a receiving a person's neck therebetween. The bottom surface 14 of the body 12 and shoulder portions 18 can be contoured to conform to a person's anatomy. FIG. 7A shows the apparatus 10 installed on a person for use. In some embodiments, as shown in FIGS. 9A-C, a clasp, or tie, 19' may be provided to "bridge" the shoulder portions 18' together to retain the device 10' on the user. The clasp 19' can be any suitable device such as a hook and loop fastener, snaps, buttons, adhesives, buckles, belts, hooks, or other mechanical fasteners.

Figure 8:
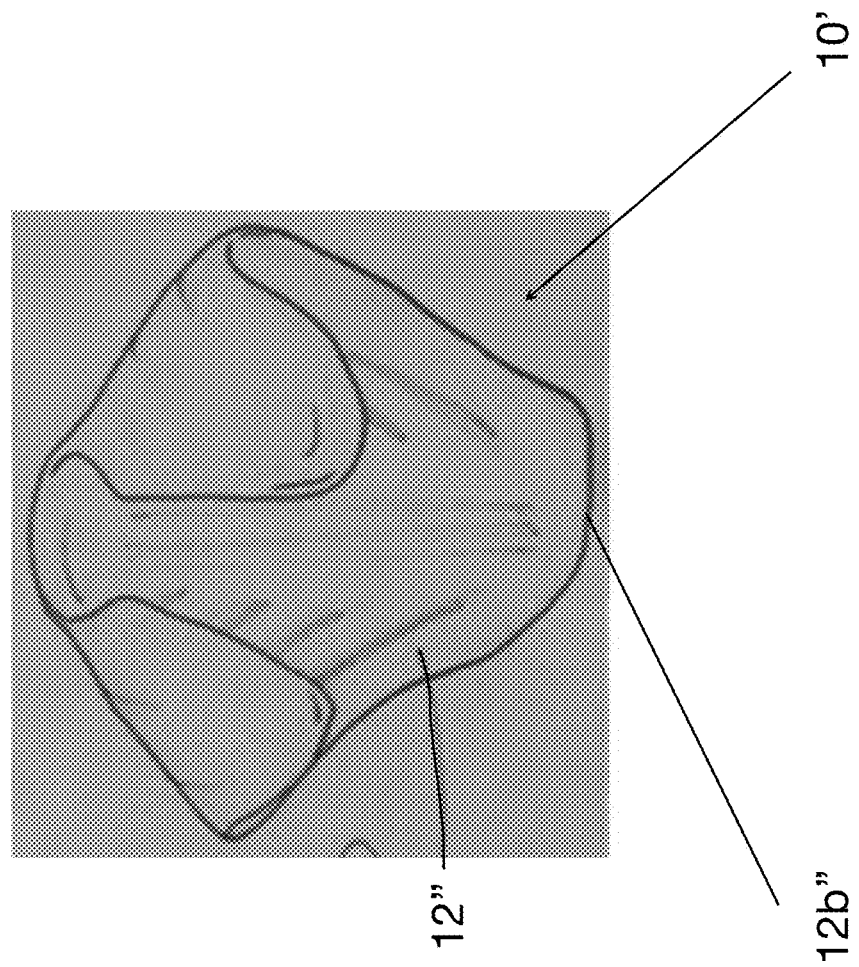
FIG. 8 is a perspective view of an alternative exemplary embodiment.

In an alternative embodiment, as shown in FIG. 8, the bottom edge 12b'' of the body 12'' can extend further downward such that a larger portion of the user's back, or front, can be treated with light, as will be discussed above. In a further alternative, the bottom surface can be higher up, if only a small area requires treatment.

Figure 7B:
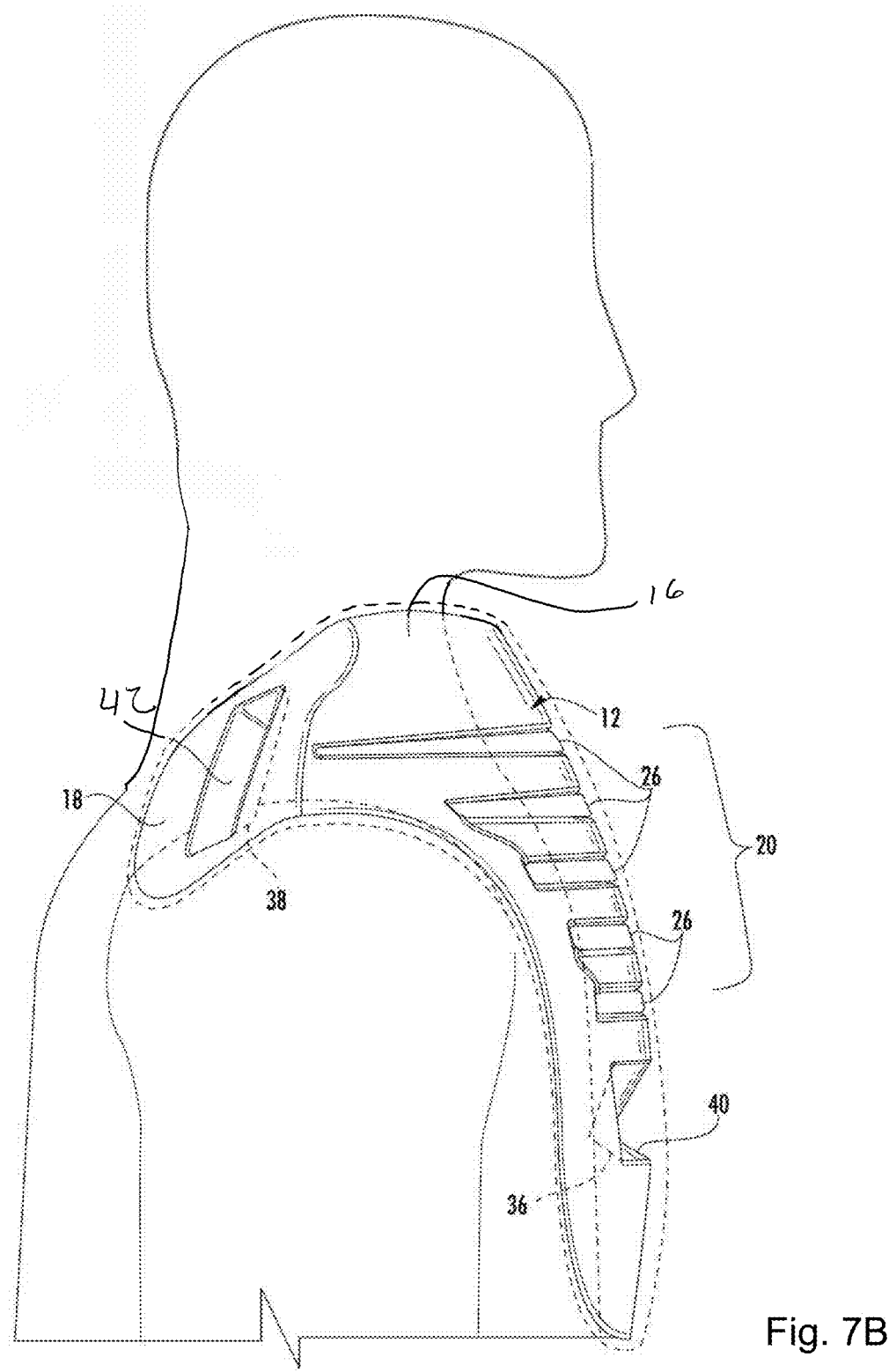
FIG. 7B is a side view of an exemplary environment with the apparatus in place on a person in an alternative orientation.

A lighting component 20 is configured and arranged to emit a light from the bottom surface 14 of the body portion 12 and forwardly extending left and right shoulder portions 18. In use, as seen in FIG. 7, the person places the left and right shoulder portions 18 on their shoulders with the body portion 12 hanging downwardly against the person's back, wearing the body portion 12 like a cape. Alternatively, the apparatus 10 can be worn with the left and right shoulder portions 18 on their shoulders with the body portion 12 hanging downwardly against the person's chest, wearing the body portion 12 like a bib, as shown in FIG. 7B.

Figure 1:
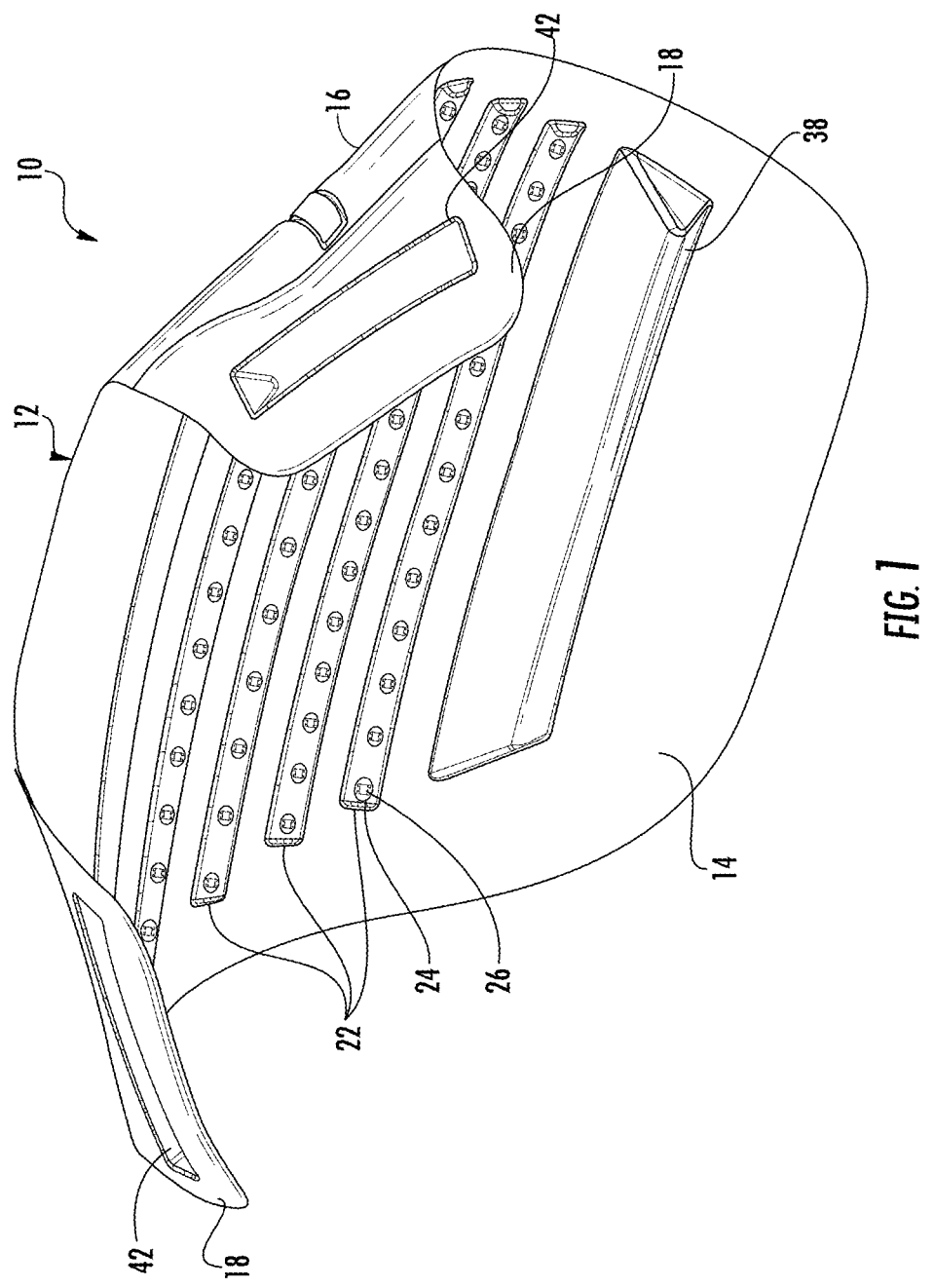
FIG. 1 is a front perspective view of an exemplary embodiment of the phototherapy apparatus.
Figure 2:
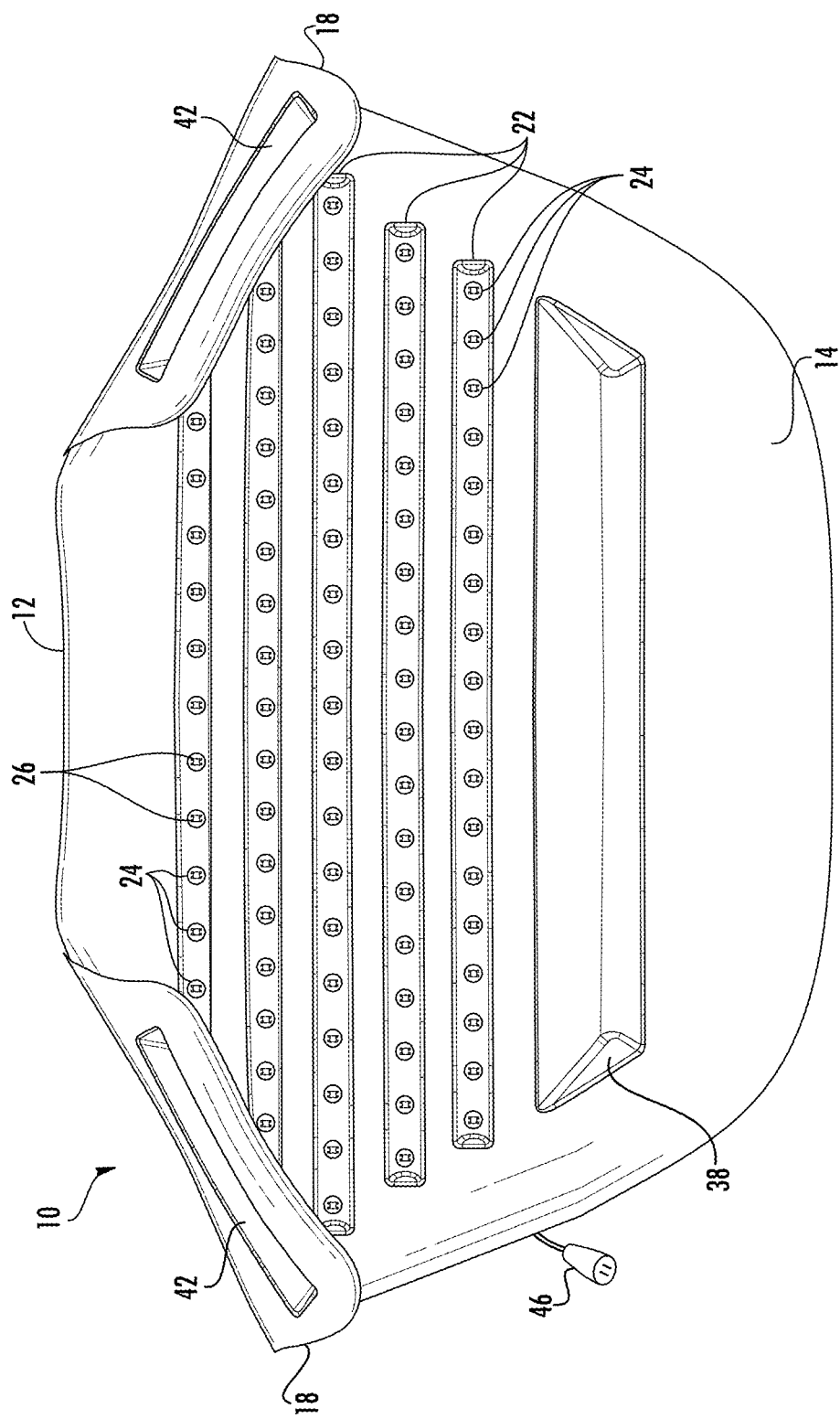
FIG. 2 is a front elevational view of an exemplary embodiment of the phototherapy apparatus.
Figure 3:
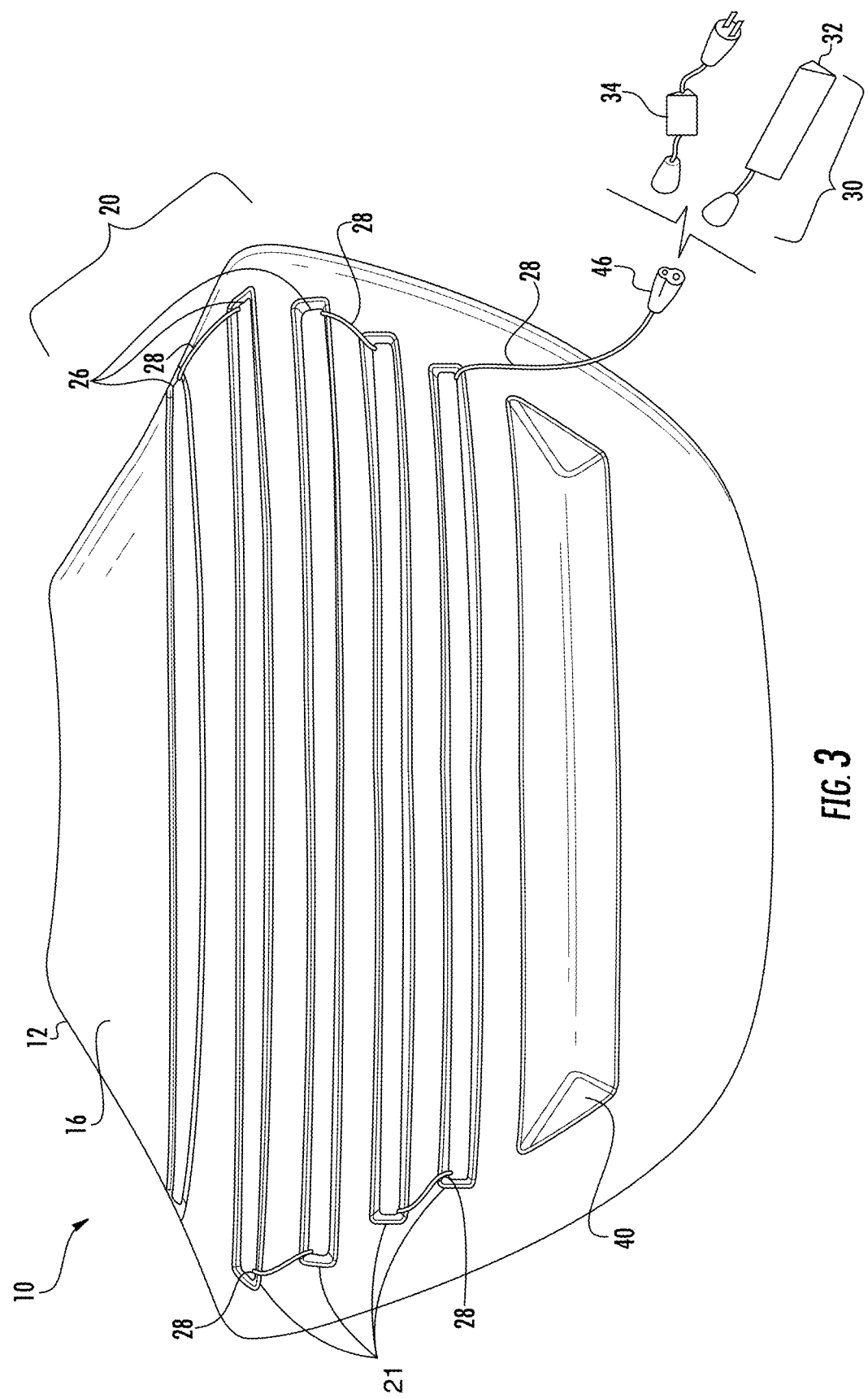
FIG. 3 is a rear elevational view of an exemplary embodiment of the phototherapy apparatus.
Figure 4:
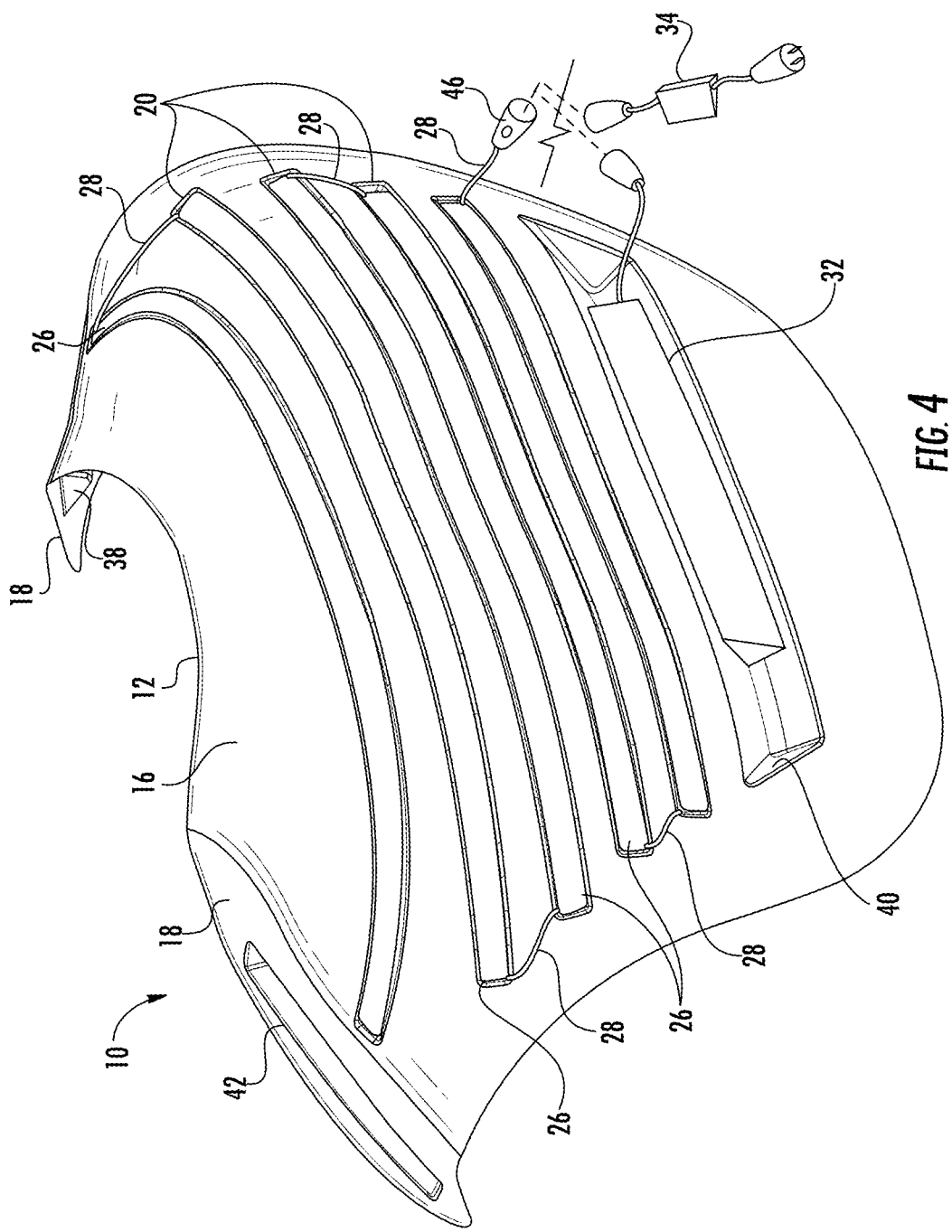
FIG. 4 is a rear perspective view of an exemplary embodiment of the phototherapy apparatus.
Figure 5:
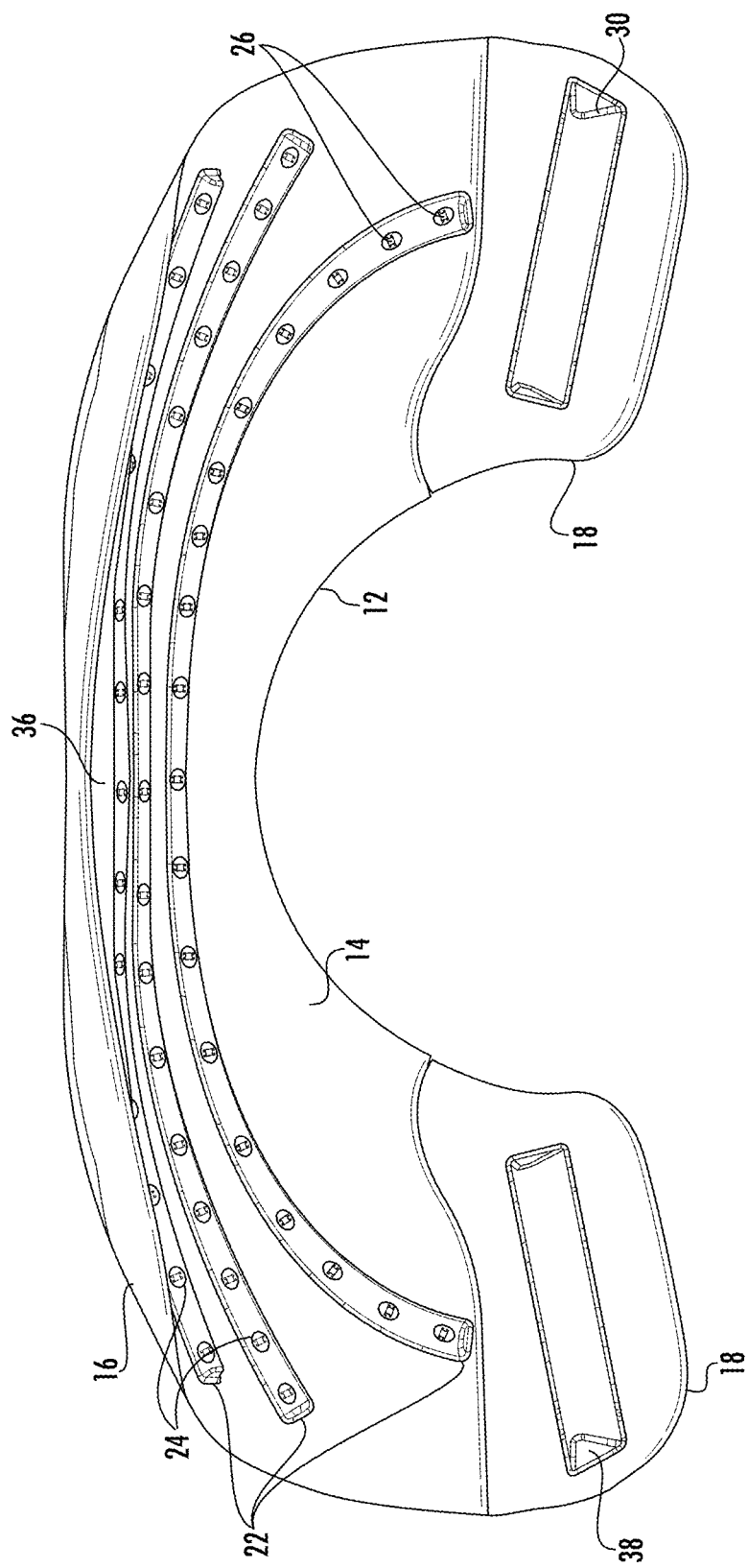
FIG. 5 is a bottom view of an exemplary embodiment of the phototherapy apparatus.
Figure 6:
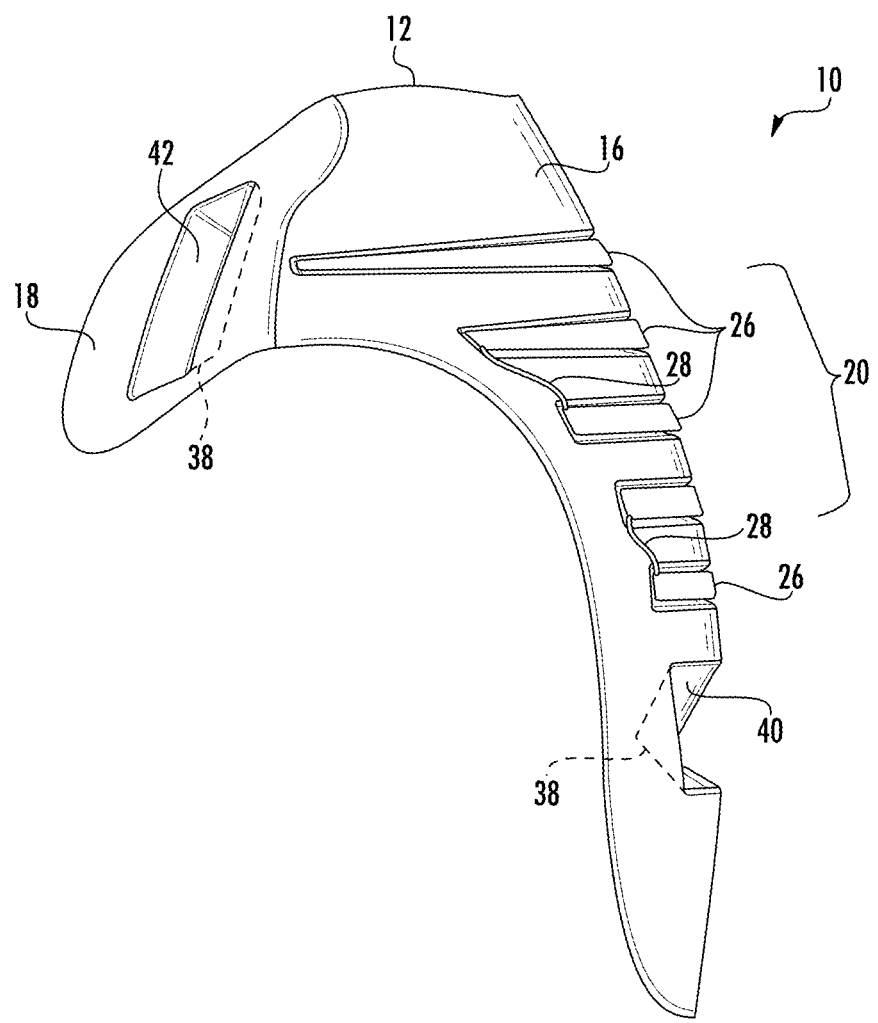
FIG. 6 is a side view of an exemplary embodiment of the phototherapy apparatus.

The apparatus 10 may include one or more grooves 21 on the top surface 16 of body portion, as best seen in FIGS. 3, 4 and 6. The grooves 21 may extend laterally in a trough-like manner on the body portion 12 and extend onto the shoulder portions 18. On the bottom surface 14 of the body portion 12, the grooves 21 may appear as projections 22. Each groove 21 preferably includes one or more apertures 24. In particular, the apertures 24 pass through the floor of the trough-like grooves 20. Residing within each groove 21 are one or more lighting elements 26 configured to emit light through the apertures 24 of the grooves 21 and out the bottom surface 14 of the body and shoulder portions 12, 18 so that the light may, in turn, be directed onto the body of the user. The grooves 20 may be mirrored to help direct light through the apertures 24 to the user. Together, the lighting elements 26 form the lighting component 20. The lighting elements 26 and the depth of the grooves 21 are configured so that the lighting elements reside fully within the grooves so that the rear surface of the apparatus is substantially flush or flat for a clean and aesthetically pleasing appearance. This facilitates the finishing of the product as will be discussed in detail below.

In some embodiments, the lighting elements 26 may be a plurality of light emitting diodes (LEDs) mounted on a flexible strip and electrically connected together. The multiple lighting elements 26, such as those in different grooves 21, may be further interconnected together via wires 28, as seen in FIG. 3. To operate the lighting component 20, the lighting elements 26 are connected to a power source 30, such as batteries 32 or a power supply 34. The batteries or battery pack 32 or power supply 34 by be internal or external to the body portion 12. In some embodiments, a controller 46 may be connected between the lighting elements 26 and power source 30, as described further below and seen in FIG. 3, for example. In some embodiments, the lighting elements 26 of the lighting component 20 are configured to emit non-UV light. In some embodiments, the lighting elements 26 of the are lighting component 20 are preferably configured to emit blue light in wavelengths between about 380 to about 500 nm, for example.

Figure 10:
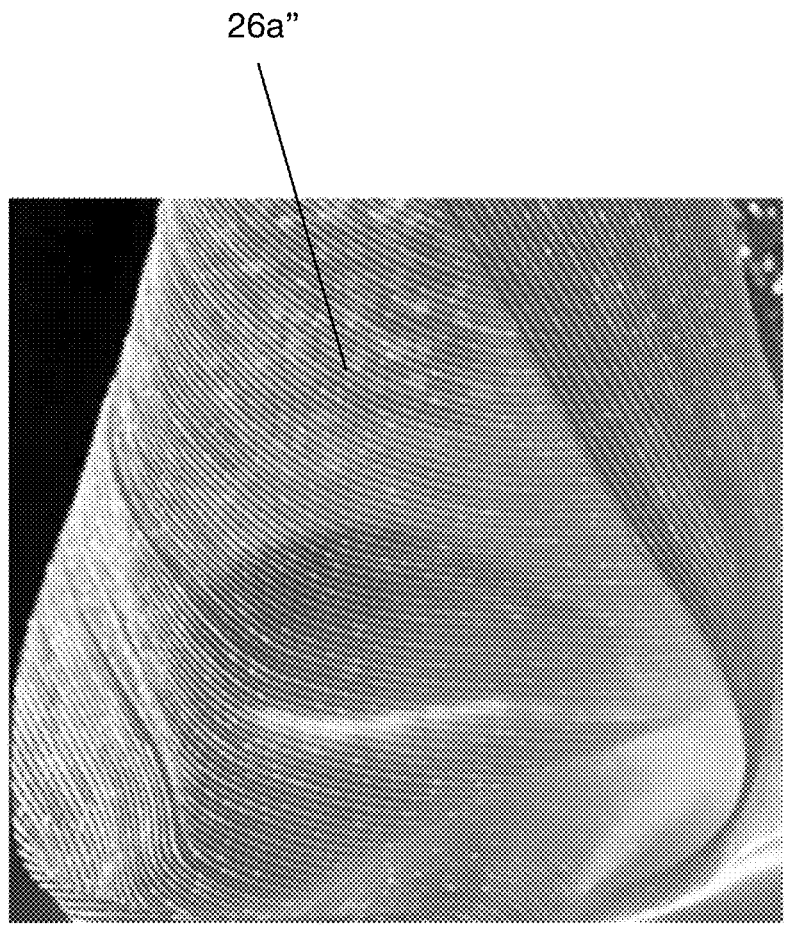
FIG. 10 is a perspective view of an alternative light source.

In an alternative embodiment shown in FIGS. 9a-9c, the lighting element 26' can be in the form of a plurality of panels 26a', 26b'. While the panels 26a' are shown in a triangular shape, they can have any shape. Similarly, the panels 26b' are shown in a generally rectangular shape, though that can have any shape. The panels 26a', 26b' may be flush with the bottom surface 14', or alternatively, they can be disposed in trenches (not shown) similar to the grooves 21 as shown in FIGS. 1-7. In the alternative embodiment that includes trenches, the trenches can have trough-like grooves to receive the panels 26a', 26b', can be mirrored, and can include various apertures to allow light out. Alternatively, the panels can be disposed on the top surface 16' of the body 12' and the body 12' can be semi or fully transparent or opaque to permit certain wavelengths of light therethrough. In some embodiments, the body 12' can be made from a soft or flexible material. The panels may provide for a larger concentration of light if needed for a given treatment plan. In a further alternative, shown in FIG. 10, the lighting element 26" can be in the form of a sheet 26a" of LEDs which can be disposed on the interior, or exterior, surface. Such a sheet 26a" can cover the entirety of the body of the device to provide an even higher intensity, or concentration of light.

The apparatus 10 also preferably includes one or more standoffs 36, 38 extending from a lower portion the bottom surface 14 of the body portion 12 and shoulder portions 18. The standoffs 36, 38 elevate the bottom surface 14 of the body portion 12 away from the person wearing the apparatus 10, as best seen in FIG. 7A, thereby allowing light emitted from the lighting component 20 to cover a larger area of the person's skin. In some embodiments, the standoffs 36, 38 form recesses 40, 42 on the top surface 16 of the body portion 12 and shoulder portions 18. In some embodiments, the recess 40 on the body portion 12 may be used to hold batteries 32 or the power supply 34 for the lighting component 20, best seen in FIG. 4.

The body portion 12 and forwardly extending shoulder portions 18 may be unitarily molded as a single piece.

As seen in FIG. 7A, the apparatus 10 preferably includes an outer covering 44, enclosing the apparatus 10 to hide the internal components and make it a more visually appealing finished product. The covering 44 may be made of fabric or layers of fabric and padding. The portion of the covering 44 that covers the bottom surface 14 of the body portion 12 may include either a window around the apertures 20 for the lighting elements 26 of the lighting component 20 or allow light to transmit through from the lighting component.

Figure 11:
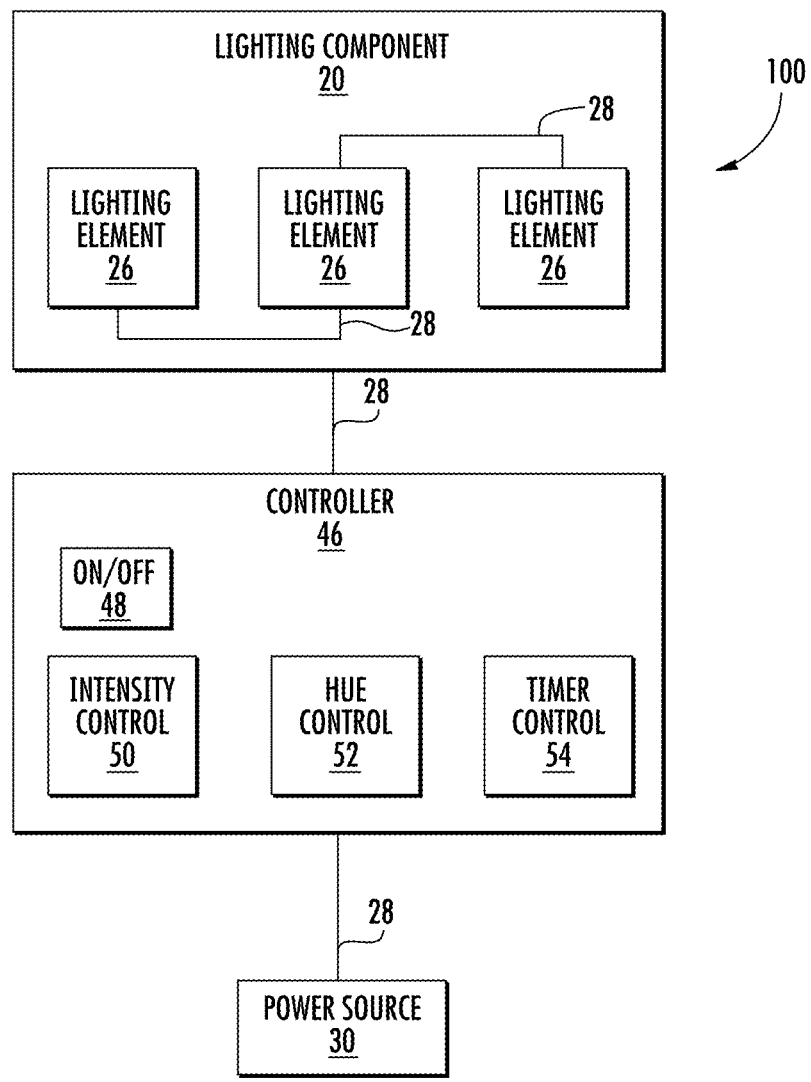
FIG. 11 is a diagram illustrating a controller for apparatus.

Referring to FIG. 11, a diagram illustrating an embodiment of the phototherapy apparatus 10 is shown generally at 100, that further includes a controller 46. The controller 46 controls power from the power source 30 to the lighting elements 26 of the lighting component 20. The controller 46 may include a switch 48 to control whether the lighting component 20 is on or off. The controller 46 may further include an intensity control 50 configured to control the brightness or lumen output of the lighting elements 26 of the lighting component 20. For example, the intensity control 50 may adjust the lumen output, variably or in stepped increments, between 1,000 and 20,000 lumens. The controller 46 may also include a hue control 52 to control the wavelength or wavelengths of light emitted by the lighting elements 26 of the lighting component 20. For instance, the hue control 52 may adjust the lighting elements 26 to emit blue light in a wavelength of 420 nm, by way of example and not limitation. The controller 46 may also include a timer control 54 configured to operate the lighting elements 26 of the lighting component 20 for a selected or predetermined time and then shut off the lighting elements 26, such as presets in five, ten, fifteen, twenty, twenty-five and/or thirty minute increments, or anywhere from zero to sixty minutes, by way of example and not limitation. It should be noted that the controller 46 may be integrated with the lighting component 20 and/or power source 30. Moreover, any associated variables of the light source can be modified or changes as a particular patient's therapy requires. For example, the controller 46 can additionally control the light wavelength, pulse duration, pulse frequency, light fluence, and light irradiance. The controller can be handheld or integrated into the device 10 itself. In a further alternative, the controller 46 can include local memory to record the number of sessions and the type of session performed so that the data can be reviewed at a later date. Further, the controller 46 can include wired or wireless connections to an external computer, tablet, or smart phone to access data and controls remotely. The foregoing is an example of how the delivery of light to the user of the apparatus 10 can be controlled, though it may be modified as desired.

Figure 12:
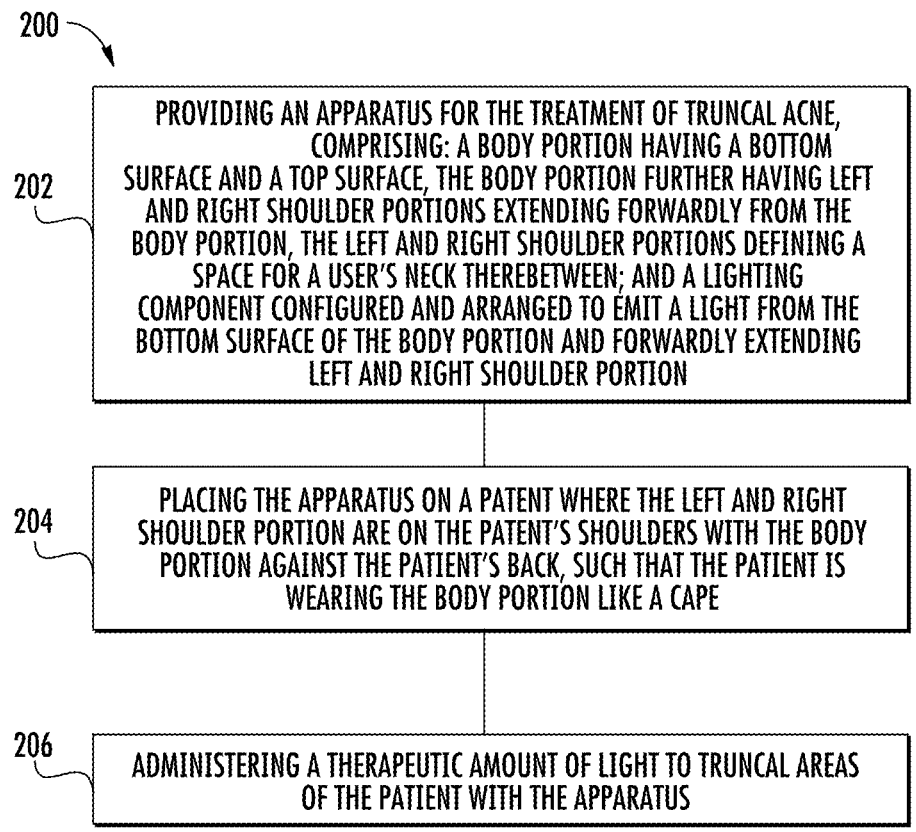
FIG. 12 is a flowchart of a method of treatment of truncal acne using the phototherapy apparatus of the present invention.

Referring to FIG. 12, a flowchart illustrating a method of treatment using the apparatus 10 is illustrated generally at 200. In a first step 202, the user (or patient) is provided with an embodiment of the apparatus 10 as described generally herein. In a second step 204, the user (or patient) places the apparatus 10 on a patient where the left and right shoulder portions 18 are on the patient's shoulders with the body portion 12 against the patient's back, such that the patient is wearing the body portion 12 like a cape. In an alternative step 204, the body portion 12 can be placed over the chest of the patient to treat the chest area. In the alternative step 204, as shown in FIG. 7B, the body portions 12 can placed on the patient such that the patient is wearing the body portion like a bib. In a third step 206, the user (or patient) administers a therapeutic amount of light to truncal areas of the patient with the lighting component 20 of the apparatus 10. As used above "user" may refer to a medical professional, such as a medical technician, clinician, nurse, nurse practitioner, physicians' assistant, dermatologist and/or physician, by way of example. Other "users" may include licensed and unlicensed salon operators and others authorized to apply phototherapy treatments, including the patient themselves.

During the administration step 206, a therapeutic amount of light for about twenty to about thirty minutes may be administered. Furthermore, this process may be repeated at intervals, such as daily, weekly, biweekly and/or monthly, as determined by the treatment regimen.

The step of administering a therapeutic amount of light 206, may further include selecting a desired light intensity and wavelength with the controller 46, via the intensity and hue controls 50, 52. The intensity and hue controls can include certain presets which can correspond to a prescribed light type and light intensity that would be required to treat the particular ailment that the patient is suffering from. In some alternative embodiments, the light source may include a plurality of light sources (not shown) each of varying wavelengths. The controls can be programmed to turn on one or more of the plurality of light sources to treat particular skin ailments as needed.

Figure 13:
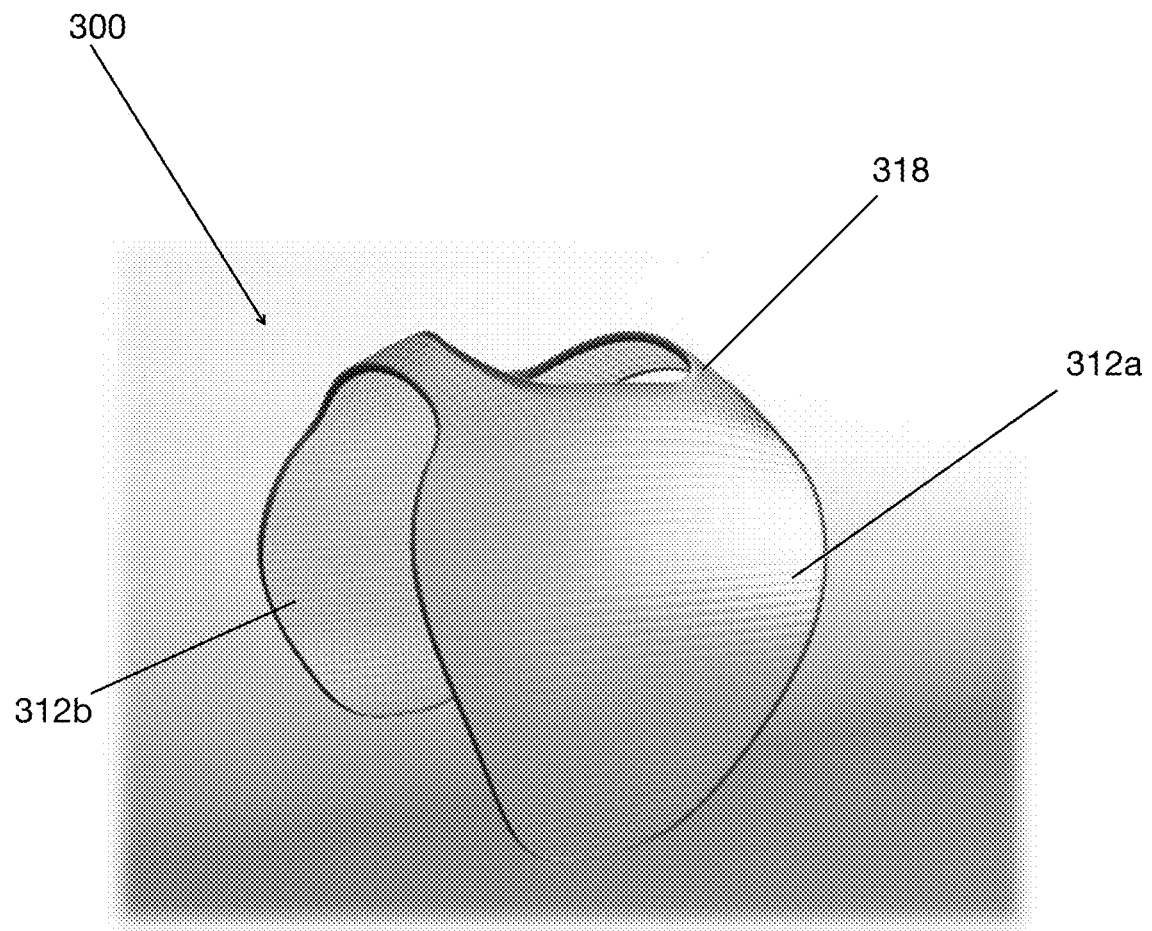
FIG. 13 is a perspective view of yet another alternative exemplary embodiment.

In an alternative embodiment of a device, as shown in FIG. 13, a two-sided body device 300 can be provided. In the illustrated embodiment, two full panel body portions 312a, 312b are shown, each structurally similar to the body portion 12 of the embodiment of FIG. 1. Both body portions 312a, 312b can include light sources to direct therapeutic light towards the back and the front of the torso at the same time. In the illustrated embodiment the body portions 312a, 312b are mirrors of one another in terms of size and shape, but that need not be the case. In an alternative embodiment, the front body 312a can be longer the back body 312b, or vice versa. The front and back body portions 312a, 312b can be attached via shoulder portions 318. The two-sided device 300 may, or may not, include stand-offs (not shown) or any of the alternative light sources (not shown). A controller can additionally be included to independently control the light sources disposed on the front and back body portions 312a, 312b so that differing light intensities and types can be administered to the respective areas of the body.

Figure 14A:
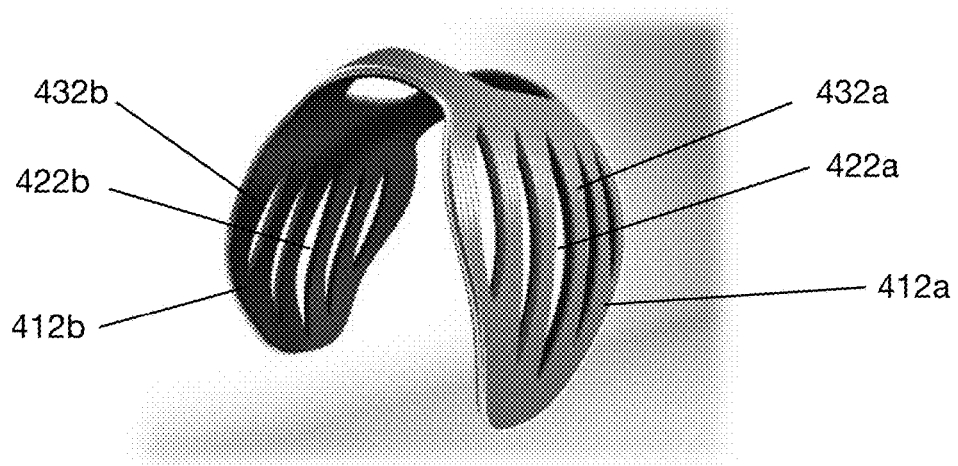
FIG. 14a is a perspective view of a further alternative exemplary embodiment.
Figure 14B:
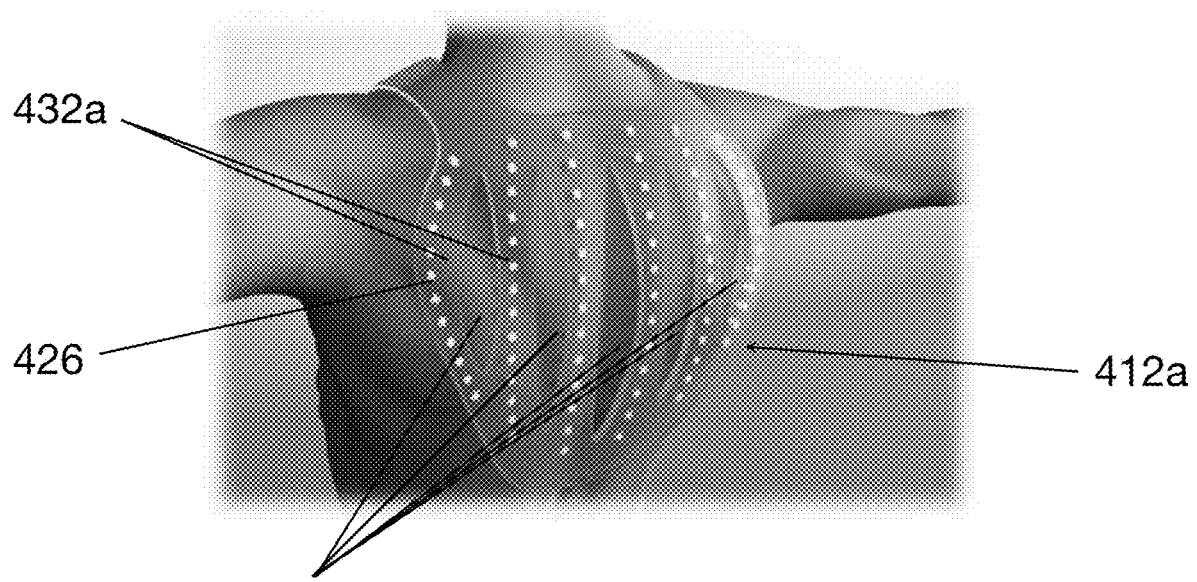
FIG. 14b is a perspective view of the apparatus of FIG. 14a in place on a person.

In a further alternative, as shown in FIGS. 14a and 14b, an alternative two-sided body device 400 can be provided. The alternative body portions 412a, 412b can be substantially the same as the body portions 312a, 312b but can include openings 422a, 422b disposed longitudinally therethrough. Such openings can advantageously reduce the weight of the device if a full light array is not required. While the openings 422a, 422b are shown extending up and downward, they can extend in any directions. Further, in the illustrated embodiment, the openings are shown having a generally oval shape, though other shapes are considered to be within the scope of the disclosure. In the illustrated embodiment five openings 422a, 422b are shown, however more or less openings may be included. Further, the same number of openings need not be included on the front and the back bodies 412a, 412b. The lights 426 can be disposed along the ribs 432a, 432b. Lights 426 can be similarly arranged on the front body 412b.

Therefore, it can be seen that the present invention provides a unique solution to the problem of providing a device and method for the treatment of truncal acne that overcomes the disadvantages and side effects of oral and topical medications and remedies taught in the prior art.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. An apparatus for the treatment of truncal acne or acne-related scarring, comprising:
    a body portion having a bottom surface and a top surface, the body portion further having left and right shoulder portions extending forwardly from the body portion, the left and right shoulder portions defining a space for a user's neck therebetween, in that the shoulder portions are contoured such that they are rounded about an axis that is angled downward, to mirror the respective left and right shoulders;
    a lighting component configured and arranged to emit a light from the bottom surface of the body portion and forwardly extending left and right shoulder portion;
    a lower standoff extending from the body portion; and
    a left shoulder standoff and a right shoulder standoff extending from the left and right shoulder portions, respectively;
    wherein the standoffs elevate the bottom surface away from a user's body when positioned thereon to distance the lighting component from the skin to optimized thorough skin coverage by the light, light intensity at the skin surface, and corresponding power supply demands,
    wherein the apparatus is configured and arranged to be placed over a user such that the left and right shoulder portion rest on the user's shoulders with the body portion against the user's back or chest, wearing the body portion like a cape or bib, and
    wherein the lighting component comprises a plurality of LEDs for the treatment of truncal acne or acne-related scarring.

2. The apparatus of claim 1, wherein the lighting component comprises a plurality of rows, arrays, or matrices of lights.

3. The apparatus of claim 1, wherein the lighting component is configured and arranged to emit phototherapeutic light of any wavelength, combination of wavelengths, intensities, pulse frequencies, and duration for the treatment of acne or acne-related scarring.

4. The apparatus of claim 1, further comprising an enclosure, encasing the body portion.

5. The apparatus of claim 1, further comprising a power supply electrically connected to the lighting component.

6. The apparatus of claim 1, further comprising a controller configured and arranged to control the lighting component.

7. The apparatus of claim 6, wherein the controller is configured and arranged to control a quality of the light emitted from the lighting component, selected from the group consisting of: duration, lumen output, pulse frequency, and wavelength(s).

8. A method of treating truncal acne or acne-related scarring, comprising:
    providing an apparatus for the treatment of truncal acne, comprising:
        a body portion having a bottom surface and a top surface, the body portion further having left and right shoulder portions extending forwardly from the body portion, the left and right shoulder portions defining a space for a patient's neck therebetween, in that the shoulder portions are contoured such that they are rounded about an axis that is angled downward, to mirror the respective left and right shoulders;
        a lighting component configured and arranged to emit a light from the bottom surface of the body portion and forwardly extending left and right shoulder portion;
        a lower standoff extending from the body portion; and
        a left shoulder standoff and a right shoulder standoff extending from the left and right shoulder portions, respectively;
    placing the apparatus on a patient where the left and right shoulder portion are on the patient's shoulders with the body portion against the patient's back or chest, such that the patient is wearing the body portion like a cape or bib and the standoffs elevate the bottom surface away from a user's body when positioned thereon to distance the lighting component from the skin to optimized thorough skin coverage by the light, light intensity at the skin surface, and corresponding power supply demands; and
    administering a therapeutic amount of light to truncal areas of the patient with the apparatus.

9. The method of claim 8, wherein the step of administering a therapeutic amount of light, comprises emitting an amount of phototherapeutic or photodynamic light to the truncal areas of the patient.

\* \* \* \* \*